US011116787B2

(12) United States Patent
Callegaro et al.

(10) Patent No.: US 11,116,787 B2
(45) Date of Patent: Sep. 14, 2021

(54) POLYSACCHARIDE COMPOSITIONS FOR TISSUE REPAIR

(71) Applicant: JOINTHERAPEUTICS S.R.L., Como (IT)

(72) Inventors: Lanfranco Callegaro, Padua (IT); Paola Brun, Padua (IT); Giulio Bianchini, Fossalta di Piave (IT)

(73) Assignee: JOINTHERAPEUTICS S.R.L., Como (IT)

( * ) Notice: Subject to any disclaimer, the term of this patent is extended or adjusted under 35 U.S.C. 154(b) by 182 days.

(21) Appl. No.: 16/306,983

(22) PCT Filed: Jun. 6, 2017

(86) PCT No.: PCT/EP2017/063639
§ 371 (c)(1),
(2) Date: Dec. 4, 2018

(87) PCT Pub. No.: WO2017/211776
PCT Pub. Date: Dec. 14, 2017

(65) Prior Publication Data
US 2020/0306288 A1    Oct. 1, 2020

(30) Foreign Application Priority Data

Jun. 7, 2016  (IT) .................. 102016000058037

(51) Int. Cl.
*A61K 31/728*   (2006.01)
*A61P 41/00*    (2006.01)
*A61K 31/702*   (2006.01)
*A61K 31/722*   (2006.01)

(52) U.S. Cl.
CPC .......... *A61K 31/728* (2013.01); *A61K 31/702* (2013.01); *A61K 31/722* (2013.01); *A61P 41/00* (2018.01)

(58) Field of Classification Search
None
See application file for complete search history.

(56) References Cited

U.S. PATENT DOCUMENTS 7,842,487 B2 * 11/2010 Hollander ........... A61L 27/3852
                                                    435/177
8,383,157 B2 *  2/2013 Muzzarelli ............. A61K 8/736
                                                    424/488

FOREIGN PATENT DOCUMENTS

| CN | 101897990 B   | 1/2013  |
| CN | 102210885 B   | 8/2013  |
| WO | 2007135116 A1 | 11/2007 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Chen Q., et al., "Original article chitosan inhibits fibroblasts growth in Achille's tendon via TGF-beta1/Smad3 pathway by miR-29b" Int. J. Clin. Exp. Pathol, Jan. 1, 2014.
D'Amelio N., et al., "Insight into the molecular properties of Chitlac, a chitosan derivative of tissue engineering", Journal of Physical Chemistry Part B: Condensed Matter Materials, Surfaces, Interfaces & Biophysical, vol. 117, No. 43, Oct. 31, 2013, pp. 13578-13587.
Donati I., et al., "Turning supramolecular structuring at the nanoscale level: nonstoichiometric soluble complexes in diluted mixed solutions of alginate and lactose-modified chitosan (Chitlac)", Biomacromolecules, vol. 8, No. 5, May 1, 2007, pp. 1471-1479.
Risbud M., et al., "Growth modulation of fibroblasts by chitosan-polyvinyl pyrrolidone hydrogel: implications for wound management?" Journal of Biosciences, Indian Academy of Science, IN vol. 25, No. 1, Mar. 1, 2000, pp. 25-31.
Search Report and Written Opinion of PCT/EP2017/063639 dated Sep. 26, 2017.

* cited by examiner

*Primary Examiner* — Dale R Miller
(74) *Attorney, Agent, or Firm* — Silvia Salvadori, P.C.; Silvia Salvadori

(57) ABSTRACT

The present application describes polysaccharide compositions that can be used as modulators of cell proliferation processes and their use in tissue repair with fibrotic process inhibition. These modulation properties can be usefully used in tissue repair for the prevention of fibrotic processes and/or tissue adhesions in traumatic, post-surgical and chronic fibrotic processes associated to autoimmune diseases.

15 Claims, 10 Drawing Sheets

POLYSACCHARIDE COMPOSITIONS FOR TISSUE REPAIR

FIELD OF THE INVENTION

The invention relates to polysaccharide compositions comprising a water-soluble mixture of polysaccharides useful as modulators of cell proliferation processes and their use in tissue repair with fibrotic process inhibition. These modulation properties can suitably be used in tissue repair and for the prevention of fibrosis and/or tissue adhesions.

PRIOR ART

The extracellular matrix is a dynamic collection of molecules interacting with each other and plays a key role in the regulation and modulation of cellular functions in tissue repair processes. In these repair processes, following trauma of various origins, a sequence of events occurs that involves different cell types, from macrophages to vascular endothelial cells to fibroblasts, all surrounded by an extracellular matrix composed of a multiplicity of components such as fibronectin, collagen, proteoglycans and glycosaminoglycans (e.g. hyaluronic acid), which have many functions of cell regulation. Collagen is recognized as the most abundant component of the extracellular matrix. The connective cells, such as fibroblasts and synoviocytes, are the cells involved especially during tissue remodeling needed for repairing, and thus primarily in the synthesis and degradation of extracellular matrix proteins, among which type I and type II collagen predominate. Their functional regulation at this stage appears crucial, since if this synthesis is excessive and not counter-balanced by collagen degradation processes, collagen production by these cells leads to the formation of fibrotic tissues. Fibrosis consists basically in an excessive deposition of cellular matrix components with pathological consequences on tissue architecture and its functions (Mutsaers SE et al., Int J Biochem Cell Biol, 1997, 29, 5-17).

In tissue repair, such as after surgical interventions, it is necessary to intervene in both the restorative phase with the promotion of cell proliferation and migration, and also in tissue remodeling by preventing the excessive deposition of extracellular matrix, especially collagen, in order to prevent fibrotic processes underlying tissue adhesion and hypertrophic scarring.

Among the molecules forming the extracellular matrix are glycosaminoglycans which, as is known, are involved in a large number of both normal and pathological biological processes of tissue repair involved cells. Such biological processes include: migration, adhesion, differentiation and proliferation.

Glycosaminoglycans are unbranched biopolymers composed of repeating disaccharide units with high hydrophilicity and they behave as polyanions at physiological due to the presence of carboxyl groups or sulfates on the saccharide residues. This allows them to adopt conformations suitable for the formation of compression-resistant matrices with rheological characteristics of high viscosity and/or viscoelasticity. Among these biopolymers, hyaluronic acid (also known as sodium hyaluronate, or HA) is the simplest, consisting of repeating units of N-acetylglucosamine and glucuronic acid. Its molecular weight can range from 400 daltons (disaccharide) o over 10 million daltons and is present in many tissues and body fluids of mammals, such as the dermal layer of the skin, the joint cartilage, the endobulbar fluids of the eye, where it is a key element for organizing other molecules and therefore also in the formation of the extracellular matrix. Also, in the connective tissue, the hydration associated with hyaluronic acid determines a suitable environment for cell motility and proliferation.

It is also known that hyaluronic acid, as endogenous biopolymer, has a role in cell motility and adhesion mediated by a surface receptor, RHAMM (Receptor for Hyaluronan-Mediated Motility), and by the transmembrane receptor CD44. From what briefly described above, therefore, it is apparent that hyaluronic acid has a key role in biological processes associated with tissue repair (Jiang D, Liang J, Noble PW, Annu Rev. Cell Dev Biol, 2007, 23, 435-61).

The peculiar physical and biological activities, together with the high biocompatibility and biodegradability by endogenous hyaluronidase, have led to an extensive use of this biopolymer with applications in cosmetics, ophthalmics, rheumatology, transport of active ingredients, in tissue repair and tissue engineering.

An essential aspect in the use of hyaluronic acid is its average molecular weight, in fact hyaluronic acid is a polymer consisting of fractions having different molecular weights and this technical feature is responsible of the physical properties thereof, which are in turn essential for the biological effects (EP 0138572; WO 2010/003797).

The viscous and/or viscoelastic properties, in particular, have been the basis for its use in visco-supplementation in osteoarticular diseases, use that has above all concerned fractions of high molecular weight hyaluronic acid (over 2000 kDa), the high molecular weight fractions having a high viscoelastic modulus in addition to high viscosity.

In addition to hyaluronic acid, other polysaccharides have also been attracting attention for an application use for their biocompatibility and their relatively high availability, such as chitosan, which is a biopolymer of particular interest.

In fact, chitosan is a polysaccharide widely available in nature, being obtainable through chemical deacetylation of chitin, and is composed mainly of glucosamine units and N-acetyl-glucosamine units residual from the chitin deacetylation treatment. Unlike hyaluronic acid, it behaves as a polycation due to the presence of amino groups of glucosamine derived from chitin deacetylation.

To date, it is known that chitosan can play a role in cellular regulation according to mechanisms still under investigation. On the knee cartilage of rats, for example, chitosan has shown to be able to induce the formation of fibrous tissue, the proliferation of chondrocytes and to reduce the decrease of the epiphyseal cartilage thickness (Jian Xi Lu et al., 1999, 20, Biomaterials, 1937-1944).

In addition, hydrogels formed of a polymer per se devoid of biological activity, such as polyvinyl pyrrolidone in combination with chitosan have shown an interesting modulation activity on different cell types. In particular, these hydrogels have shown to be able to inhibit the growth and proliferation of fibroblasts and to induce the rooting and growth of epithelial cells.

It is to be noted, however, that chitosan alone has shown the ability to induce a decrease in the growth of epithelial cells (Risbud M et al., J Biosci, 2000, 25, 25-31). This effect of cell growth inhibition of chitosan was also confirmed in an Achilles tendon injury model where chitosan has shown to be able to induce an inhibition of fibroblasts growth, acting on cell adhesion processes which is significant in post-surgical sequelae of these diseases (Qiang Chen et al, Int J Clin Exp Pathol, 2014, 7, 8462-8470).

However, the greatest problem in the use of chitosan is its low solubility in water which requires pH equal or lower than 5. The lowering of pH involves the protonation of amino groups of glucosamine residues, thus imparting solubility to the system. In addition, in relation to its high positive charge in aqueous solutions, it is poorly compatible with polyanionic polymers, resulting in coacervates with phase separation.

In connection with its wide use, chitosan has become one of the most studied polysaccharides from a chemical point of view in order to improve its useful properties for application purposes, in particular its viscosity and solubility in water. In recent years, several chitosan derivatives have been obtained through chemical modifications of the polymer chain. Commonly, reactions of the amino residues of glucosamine units are used for these modifications. In particular, the introduction of saccharide units (mono- and oligosaccharides) in the side chain allowed to achieve water soluble chitosan derivatives without the need of lowering the pH to acidic values, therefore avoiding consequent polymer degradation problems. The derivatization of chitosan with side saccharide groups, for example by the insertion of lactose units obtained by a reductive amination reaction has entailed, as reported in U.S. Pat. No. 4,424,346 (Hall, L. D. and Yalpani, M.), a greater solubility of the derivatives of this polysaccharide in water and it is precisely in these derivatized forms that chitosan takes the most favorable properties for use as a high biocompatibility biomaterial. In addition, such a derivatization improves the compatibility of chitosan in aqueous solutions with polyanionic biopolymers, such as alginic acid and hyaluronic acid (EP 2021408). Mixtures of these polymers have shown to produce homogeneously dispersed aqueous solutions without the formation of coacervates characterized by viscosity and viscoelasticity higher than those of the starting polysaccharides.

The chitosan oligosaccharide derivative obtained by the functionalization of the amino group of glucosamine with lactose has also shown interesting properties from a biological point of view. In particular, two derivatives with different degree of functionalization were able, unlike the unmodified chitosan, to induce the cellular aggregation of chondrocytes and stimulate the production of glycosaminoglycans and collagen through an interaction with galectin-1 (Donati et al., Biomaterials, 2005, 26, 987-998; Marcon P. et al., 2005, 26, 4975-4984). This activity is also maintained when the oligosaccharide derivative of chitosan with lactose is combined in hydrogels with anionic polysaccharides, such as alginic acid (Macleod E. et al., J Biomed Mat Res Part A, 2007, DOI:10.1002/jbm.a31307).

In the field of tissue repair, it is strongly felt the need for instruments able to induce a balanced repair of the affected tissues without the formation of fibrotic and/or adhesion processes and in order to meet this need, the use of hyaluronic acid has long been studied for its viscoelastic properties alone or in combination with other compounds.

For example, EP 059015 describes compositions comprising a fibrin- and fibrinogen-based glue combined with biodegradable and biocompatible polymers capable of increasing the viscosity of the compositions. Preferably, these polymers are selected among proteoglycans and polysaccharides, including hyaluronic acid, and for the purposes of the invention such polymers must have a high molecular weight. Of these polymers, therefore, the only physical property is exploited, and in fact, these polymers are defined as "viscosity enhancing polymers". This concept has long been followed in the preparation of compositions suitable for preventing tissue adhesions.

In this regard, the research aimed at the development of tissue repair tools with inhibition of fibrotic and tissue adhesion processes has been directed primarily to the development of fractions of high molecular weight hyaluronic acid or its degradation-resistant derivatives by endogenous hyaluronidase for the promotion of a "barrier effect" due to the high viscosity of the compositions.

In WO 97/07833 there are described biomaterials consisting of hyaluronic acid derivatives esterified with benzyl alcohol or cross-linked as an alternative to hyaluronic acid fractions of high molecular weight and hence very viscous for use in the prevention of post-surgical adhesions. The hyaluronic acid derivatization is intended to increase its degradation resistance and to optimize the biomaterials in the form of gels, membranes, and tissues.

Similarly, EP 1207828 describes gels that can be used as anti-adhesion barriers, which are obtained by mixing a foam of cross-linked hyaluronic acid derivatives and hyaluronic acid aqueous solutions. To obtain such gel, the use of hyaluronic acid with a molecular weight in the range of 1000 kDa to 2000 kDa is indicated. For this use, however, both the use of fractions of high molecular weight hyaluronic acid (e.g., from 3500 to 10000 kDa), as described in the recent patent application EP 2977460, and the use of chemically modified hyaluronic acids and in particular hydrogels consisting of structurally complex hyaluronic acid derivatives, wherein those hyaluronic acids having a molecular weight in the range of 50 to 3500 kDa are bound to biocompatible and biodegradable polyesters with a molecular weight in the range of 3 to 900 kDa, as described in WO 2012/014180., are deemed to be valid.

It should be noted, however, that due to the complexity of cellular interactions in tissue repair processes, in order to promote it without incurring in fibrotic and/or tissue adhesion processes, it is necessary to identify a strategy not exclusively based on a "barrier effect" of high molecular weight hyaluronic acid or its endogenous degradation resistant derivatives. To meet the therapeutic need, as demonstrated by long research in the field, it may be more significant to exploit the peculiar biological properties of hyaluronic acid and other biocompatible polysaccharides for therapeutic purposes, and to intervene in the modulation of the proliferation processes of the different types of cells involved in the tissue repair.

SUMMARY

The object of the present invention is to provide compositions to modulate cell proliferation processes for use in tissue repair with the inhibition of fibrotic processes, exploiting the biological properties of polysaccharide biopolymers. Therefore, an object of the present invention are polysaccharide compositions comprising hyaluronic acid and an oligosaccharide derivative of chitosan with lactose, obtained by a reductive amination reaction of D-glucosamine having a degree of substitution of the amine functional group of the same with lactose of at least 40%, for use in tissue repair and in inhibition of fibrosis and/or tissue adhesions through cell proliferation modulation.

Typically, the hyaluronic acid of the polysaccharide composition object of the invention is the matrix in which the oligosaccharide derivative of chitosan is homogeneously dispersed.

In accordance with some aspects, the compositions of the invention is for use in the tissue repair and/or for the prevention of fibrosis and/or adhesions in traumatic, post-surgical and chronic inflammatory tissue injuries.

The advantages achieved with the present invention will become more apparent to a skilled person from the following detailed description with reference to the following figures.

BRIEF DESCRIPTION OF THE FIGURES

FIGS. 4A-4B. The figure shows the results obtained in the scratch test on dermal fibroblasts treated with hyaluronic acid at a concentration of 1 mg/ml, chitlac at a concentration of 0.75 mg/ml and a mixture of the same (HA 1 mg/ml, chitlac 0.75 mg/ml) at 0, 48 and 72 hours on cell migration in % (A) and cut closing in µm (B).

DETAILED DESCRIPTION OF THE INVENTION

The oligosaccharide derivative of chitosan, obtained by reductive amination of the D-glucosamine amino functional group with lactose, of the polysaccharide composition object of the invention, hereinafter also referred to as chitlac, was evaluated in vitro on different cell types of connective tissue origin, as these cells are the most involved in issue repair and remodeling following tissue injuries. Such injuries may have various origins and may vary from surgical or traumatic injuries to those resulting from chronic inflammatory processes.

In in vitro experiments, the results of which are presented in detail hereinafter, such a derivative of chitosan substituted with lactose (chitlac) has shown to have interesting biological properties on the proliferation of cells of different origin.

In particular, both on dermal fibroblasts and synoviocytes and on human chondrocytes, it has shown a dose-dependent effect of inhibition of cell proliferation that however does not affect the cell viability.

On these cells, in fact, chitlac exerts a clear and significant dose-dependent inhibitory effect on cell proliferation following incubation for six days already at the concentration of 0.25 mg/ml. The effect is very noticeable at higher concentrations (0.75 and 1.0 mg/ml for fibroblasts and 1.0 and 1.5 mg/ml for synoviocytes and chondrocytes). After incubation for three days, however, there is no significant effect on fibroblasts, whereas the effect is significant for chondrocytes and synoviocytes at higher concentrations. Moreover, there are no significantly different effects at concentrations between 1.0 and 1.5 mg/ml. From the analysis of data, therefore, it can be seen that chitlac inhibits the cell proliferation of chondrocytes and synoviocytes after three days of incubation at concentrations of 1.0 and 1.25 mg/ml and after 6 days of incubation already at 0.25 mg/ml on all three cell types considered. The effect is therefore not only dose-dependent but also time-dependent.

From these results it is clear that chitlac inhibits the cell proliferation of any cell type, that is, both cells involved in tissue remodeling with deposition of collagen, such as fibroblasts and synoviocytes whose hyperactivity is prodromal to fibrotic processes, and on cells than have a function involved in injured tissue repair such as chondrocytes, which as known are cells involved in the formation of joint cartilage.

Unlike chitlac, hyaluronic acid (hereinafter also referred to as HA) has instead shown that it does not significantly influence the processes of cell proliferation of fibroblasts and chondrocyte at none of the concentrations employed nor any of the incubation times considered, except for an inhibitory effect already at 0.75 mg/ml and significant at the highest concentration (1.25 mg/ml) and after six days of incubation on synoviocytes. This effect does not seem to be related to a barrier effect of hyaluronic acid because the fraction of HA used has a molecular weight that is not significantly high.

For application purpose, however, the effect on cell proliferation is particularly relevant when the two polysaccharides are combined.

In fact, it should be noted that: i) the combination of HA at a concentration of 0.5 mg/ml does not significantly affect the inhibitory effect exerted by chitlac at none of the concentrations tested nor at three or six days of incubation on chondrocytes and synoviocytes; ii) the combination of HA at the concentration of 1.0 mg/ml prevents the inhibitory effect of chitlac at all concentrations totally on chondrocytes and it partially reduces the inhibitory effect of chitlac at higher concentrations on synoviocytes; iii) the combination of HA at the concentration of 1.25 mg/ml prevents the inhibitory effect of chitlac at concentrations from 0.1 to 0.75 mg/ml on chondrocytes but not at the highest concentration of chitlac and reduces the effect of chitlac but does not abolish it on synoviocytes, while on fibroblasts it does not inhibit the effect of chitlac.

The results therefore suggest that the inhibitory effect of chitlac on cell proliferation involved in the synthesis of collagen, such as fibroblasts and synoviocytes, is not abolished completely by hyaluronic acid, while the same is able to prevent it on cells whose proliferation is prodromal to tissue repair.

It was also ascertained that the inhibitory effect of cell proliferation does not change the physiological migration of dermal fibroblasts even when chitlac is used at higher concentration where the inhibitory effect of proliferation is more significant. This process therefore does not negatively affect the process of tissue repair.

Without wishing to be bound to any theory, it can be hypothesized that the two polysaccharides intervene in cellular repair and remodeling processes via differentiated mechanisms and therefore combining them results in a modulation of cell proliferation processes useful for inducing tissue repair, preventing fibrotic processes due to an overproduction of collagen.

In one aspect, the present invention therefore relates to a polysaccharide composition comprising hyaluronic acid and an oligosaccharide derivative of chitosan with lactose obtained by a reductive amination reaction of D-glucosamine having a degree of substitution of the amine functional group of the same with lactose of at least 40% for use in tissue repair and in the inhibition of fibrotic processes through cell proliferation modulation.

As is known, the two polysaccharides have good water solubility properties and are compatible with each other, since aqueous solutions of the same when mixed do not give rise to precipitates in the form of coacervates, with phase separation, due to the interactions between anionic groups of hyaluronic acid and cationic groups of amino residues still present in the oligosaccharide derivative obtained from chitosan and lactose (chitlac). They instead give compositions, especially solutions characterized by viscosity and viscoelasticity, wherein the hyaluronic acid is a matrix in which the oligosaccharide derivative chitlac is homogeneously dispersed.

In certain embodiments, the chitosan used to obtain the oligosaccharide derivative with lactose (chitlac) is obtained from various natural sources (e.g. by deacetylation of chitin) or with recombinant technology methods and has an average molecular weight (hereinafter referred to as MW) up to 1,000 kDa. The average molecular weight of the starting chitosan is preferably in the range from 500 kDa to 700 kDa and more preferably between 200 and 400 kDa. Such a chitosan preferably has a degree of deacetylation up to 90% and the preferred one has a degree of residual acetylation of between 10 and 20%.

Moreover, for the purposes of the present invention, the degree of substitution of amino groups of chitosan D-glucosamine with lactose is at least 40%. Preferably, the degree of substitution of amino groups of chitosan with such an oligosaccharide is in the range from 50% to 70% and more preferably, it is 60%.

As regards hyaluronic acid, also this polysaccharide can be obtained from various natural sources or with recombinant technology methods via fermentation. However, the average molecular weight for this polysaccharide is significant and for the purposes of the invention, it is not greater than 2,000 kDa and comprised between 1,000 kDa and 1,600 kDa, so as to have, after damp heat sterilization, a process that as known causes some degradation of the biopolymer, a hyaluronic acid with a molecular weight of between 800 kDa and 1,000 kDa.

The more important aspect of the polysaccharide compositions object of the invention is the content of the two polysaccharides because, as observed experimentally, this content has a significant effect for achieving the purposes of the invention.

In particular, hyaluronic acid in the polysaccharide compositions used for reparative purposes and for the prevention of fibrotic processes is at a concentration of 10 to 20 mg/ml (1-2% w/v) and the oligosaccharide derivative chitlac of 2.5 to 7.5 mg/ml (0.25%-0.75 w/v). Preferably, hyaluronic acid is 10 mg/ml or 12.5 mg/ml and chitlac is of 2.5 to 7.5 mg/ml. In the preferred embodiment, hyaluronic acid is 10 mg/ml while chitlac can range from 2.5 to 5 mg/ml depending on the desired effects.

According to some embodiments the compositions of the invention is used to promote tissue repair and/or prevent fibrotic processes in traumatic and post-surgical tissue lesions and chronic fibrotic processes associated to autoimmune diseases. Such uses are preferably addressed to tissue repair and fibrotic processes prevention mostly involving tissues selected from skin dermis, abdominal endothelial tissues, tendons and cartilage.

In particular, one of the use is in traumatic and post-surgical sequelae involving dermis and abdominal tissues. Yet other uses are in post-surgical sequelae of tendons and cartilage tissues and fibrotic process associated to autoimmune diseases affecting dermis and cartilage tissues, most preferably selected from psoriasis and psoriatic osteoarthritis.

In certain embodiments, the compositions object of the invention is used in combination with other ingredients and/or solvents suitable for pharmaceutical use for preparing biomaterials, suitable to be administered by topical, intradermal or intra-articular route as aqueous solutions, non-woven fabric, membranes, hydrogels or preparations obtained thereby by freeze-drying.

EXAMPLES

The experimental tests described in the examples below were performed using the following polysaccharides:

Hyaluronic acid (HA): 1-1.6 MDa (1000-1600 kDa) of appropriate pharmaceutical grade for intraarticular and intraocular administration obtained by biofermentation;

Chitlac Hydrochloride (CTL): chitlac hydrochloride was obtained by addition of aqueous hydrochloric acid to a Chitlac solution in water until pH 2.5 was reached. Subsequently, the salt of the polymer was precipitated with methanol, filtered on a sintered glass filter (gooch) and the collected solid washed with methanol (3×) and dried. Chitlac used for salt preparation is characterized by a degree of lactose replacement between 50 and 70% and was obtained from a chitosan of 200-400 kDa with a degree of residual acetylation of approximately 15%.

Known titre polysaccharide stock solutions were prepared using water for injectable solutions as described below.

Hyaluronic Acid 1% in PBS 1×: 800 mg of hyaluronic acid were dissolved in 72 mL of water for injection preparations. The solution thus obtained was added with 8 mL of 10× saline phosphate buffer (PBS 10×: NaCl 1370 mM, KCl 27 mM, Na 2 $HPO_4$ 81 mM, $NaH_2PO_4$ 17.6 mM) and then sterilized in autoclave at 121° C. for 15 minutes (EP 5.1.1).

Chitlac 1% in PBS 1×: 800 mg of chitlac hydrochloride were dissolved in 69.04 mL of water for injectable solutions and 2.96 mL of 0.5 M NaOH were added drop-wise to the solution. The solution was then added with 8 mL of 10× saline phosphate buffer (PBS 10×: NaCl 1370 mM, KCl 27 mM, $Na_2HPO_4$ 81 mM, $NaH_2PO_4$ 17.6 mM) and subsequently sterilized in autoclave at 121° C. for 15 minutes (EP 5.1.1).

Example 1

Assay on the Proliferation of Human Dermic Fibroblasts

Human fibroblasts were isolated from skin samples of healthy donor (57-62 years) undergoing plastic surgery.

In short, the skin was placed for 1 hour in sterile PBS with 3% penicillin and streptomycin, in order to break down the bacterial charge. Subsequently, the samples were cut into small pieces and placed in a dispase II solution (2.5 mg/ml HBSS, Hank's balanced salt solution) for 4 hours at 37° C., to obtain detachment of the epithelial from the underlying dermis. The dermis fragments were digested with collagenase I (80 U/ml in HBSS) for 12 hours in a 37° C. incubator, 5% pCO2. Digestion was blocked with Dulbecco's Modified Eagle's Medium (DMEM) containing 10% fetal calf serum (FCS), 4 mM glutamine, 100 IU/ml penicillin/streptavidin and the suspension was filtered and centrifuged at 1200 rpm. The fibroblasts present in the pellets were resuspended in complete DMEM medium and seeded on sterile culture plates in incubator at 37° C., with a percentage of $CO_2$ of 5% and a relative humidity of 90%.

The cell phenotype was confirmed by observing the shape of cells in the inverted optical microscope and by immunocytochemical analysis for prolyl-4-hydroxylase. The medium was changed every two days and confluent cultures were detached from the bottom of the plate with a 0.05% trypsin solution and 0.02% EDTA and subsequently divided by 1:3. For the experiments, cells from the third to the fifth passage were used.

The fibroblasts were seeded at a concentration of 2500 cells per well in a 48-well plate. The day after the sowing, the cells were treated with the substances under study at the following concentrations: hyaluronic acid (HA) 0.1 to 1.25 mg/ml; Chitlac (CTL) 0.1 to 1.0 mg/ml; a mixture of HA and CTL, consisting of a fixed concentration of 1.25 mg/ml HA and increasing amounts of CTL (0.1 to 1.0 mg/ml). The medium was renewed every two days with the substances under examination. The effects of the treatment on cell viability were analyzed after 1 day, 3 days, 6 days by MTT (4-5-dimethylthiazol-2-yl)-2,5-diphenyltetrazolium bromide assay, according to the Denizot and Lang method (Denizot et al., J Immunol Meth, 1986, 89, 271-277). This assay measures the activity of succinate dehydrogenase present in cell cellular mitochondria and is based on the reduction of (4,5-dimethylthiazol-2-yl)-2,5-diphenyltetrazole bromide to insoluble formazone salts. The amount of formazone salts produced is determined by spectrophotometry and is proportional to the amount of enzyme and hence, indirectly, to the number of vital cells.

In short, after removing the culture medium, the cell monolayers were washed with PBS and the MTT solution was added for 3 hours at 37° C. At the end of the incubation, the MTT was removed and replaced with an extraction solution (90% isopropanol, 10% DMSO) for 15 minutes at 37° C. The absorbance measurement was performed with a spectrophotometer at 570 nm.

Statistical analysis was done by two-tailed t-test and differences with a t-test value <0.05 were considered significant.

Three-fold experiments were set up and performed three times.

Figure 1:
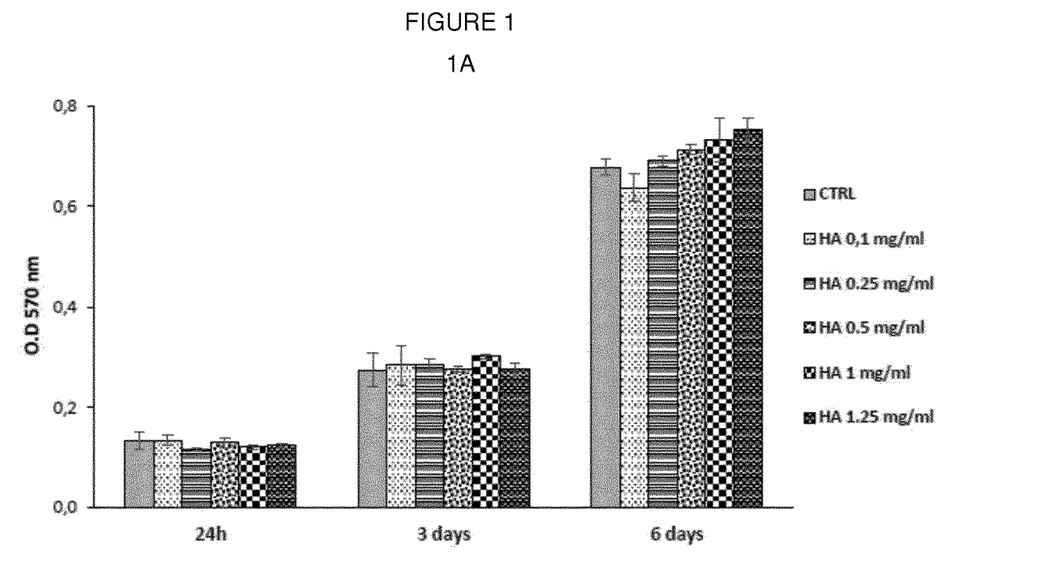
FIGS. 1A-1C. The figure shows the results obtained on the proliferation of human fibroblasts after incubation at 24 hours, 3 and 6 days with hyaluronic acid (HA), chitlac, hyaluronic acid and chitlac at different concentrations: (A) HA at the concentration from 0.1 to 1.25 mg/ml; (B) chitlac at the concentration from 0.1 to 1.0 mg/ml; (C) HA at the concentration of 1.25 and chitlac at the concentration from 0.1 to 1.0 mg/ml.

FIG. 1A and Table 1A show the results obtained on cell proliferation with hyaluronic acid at the mentioned concentrations.

TABLE 1A

|  | 24 hr | SD | 3 days | SD | 6 days | SD |
|---|---|---|---|---|---|---|
| Ctrl | 0.134 | 0.017 | 0.274 | 0.033 | 0.678 | 0.161 |
| 0.1 mg/ml | 0.135 | 0.01 | 0.284 | 0.039 | 0.637 | 0.027 |
| 0.25 mg/ml | 0.118 | 0.003 | 0.285 | 0.013 | 0.696 | 0.002 |
| 0.5 mg/ml | 0.131 | 0.01 | 0.276 | 0.006 | 0.713 | 0.009 |
| 1 mg/ml | 0.122 | 0.006 | 0.301 | 0.006 | 0.731 | 0.44 |
| 1.5 mg/ml | 0.124 | 0.004 | 0.275 | 0.014 | 0.752 | 0.023 |

FIG. 1B and Table 1B show the results obtained on cell proliferation with chitlac at the mentioned concentrations.

TABLE 1B

|  | 24 hr | SD | 3 days | SD | 6 days | SD |
|---|---|---|---|---|---|---|
| Ctrl | 0.116 | 0.004 | 0.271 | 0.015 | 0.662 | 0.003 |
| 0.1 mg/ml | 0.121 | 0.013 | 0.266 | 0.025 | 0.598 | 0.058 |
| 0.25 mg/ml | 0.133 | 0.018 | 0.289 | 0.027 | 0.554 | 0.026 |
| 0.5 mg/ml | 0.139 | 0.011 | 0.274 | 0.027 | 0.512 | 0.031 |
| 1 mg/ml | 0.130 | 0.008 | 0.270 | 0.011 | 0.406 | 0.043 |
| 1.5 mg/ml | 0.127 | 0.002 | 0.282 | 0.009 | 0.370 | 0.024 |

FIG. 1C and Table 1C show the results obtained on cell proliferation with hyaluronic acid at a concentration of 1.25 mg/ml and chitlac at concentrations increasing from 0.1 to 1.0 mg/ml at the mentioned concentrations.

TABLE 1C

| CHITLAC | 24 hr | SD | 3 days | SD | 6 days | SD |
|---|---|---|---|---|---|---|
| Ctrl | 0.100 | 0.002 | 0.300 | 0.001 | 0.627 | 0.002 |
| 0.1 mg/ml | 0.114 | 0.008 | 0.273 | 0.021 | 0.579 | 0.006 |
| 0.25 mg/ml | 0.129 | 0.016 | 0.289 | 0.002 | 0.471 | 0.025 |
| 0.5 mg/ml | 0.127 | 0.012 | 0.241 | 0.046 | 0.401 | 0.028 |
| 0.75 mg/ml | 0.122 | 0.003 | 0.238 | 0.029 | 0.345 | 0.039 |
| 1.0 mg/ml | 0.122 | 0.008 | 0.231 | 0.043 | 0.328 | 0.014 |

Example 2

Assay on Proliferation of Articular Cartilage Chondrocytes

Human chondrocytes have been isolated from a cartilage biopsy taken from patients undergoing surgery to replace the knee cartilage.

The biopsy was finely cut and then transferred to a 0.25% trypsin solution for 15 minutes at 37° C. At the end, the cartilage was transferred to a I 300 U/ml collagenase solution for 12 hours in a 37° C. incubator, 5% pCO2. After filtration, the solution was centrifuged at 1200 rpm and the pellet cells re-suspended in Dulbecco's Modified Eagle's Medium (DMEM) completed with 10% fetal calf serum (FCS), 4 mM glutamine, 100 IU/ml penicillin/streptavidin, in presence of 50 mg/ml of ascorbic acid. The cells were kept in culture by changing the medium every two days. At confluence, the cells were detached from the bottom of the culture plate with a 0.05% trypsin solution and 0.02% EDTA, divided by 1:3 and used for experiments from the second to the third step.

The chondrocytes were seeded at a concentration of 3000 cells per well in a 48-well plate. The day after the sowing, the cells were treated with the substances under study at the following concentrations: CTL 0.1 to 1.5 mg/ml; HA 0.1 to 1.25 mg/ml; a mixture of HA and CTL, consisting of a fixed concentration (0.5 mg/ml, 1 mg/ml or 1.25 mg/ml) of HA and variable amounts of CTL. The medium was renewed every two days with the substances under examination.

The effects of the treatment on cell viability were analyzed after 1 day, 3 days, 6 days by MTT (4-5-dimethylthiazol-2-yl)-2,5-diphenyltetrazolium bromide assay, according to the Denizot and Lang method as in the previous example.

In short, after removing the culture medium, the cell monolayers were washed with PBS and the MTT solution was added for 3 hours at 37° C. At the end of the incubation, the MTT was removed and replaced with an extraction solution (90% isopropanol, 10% DMSO) for 15 minutes at 37° C. The absorbance measurement was performed with a spectrophotometer at 570 nm.

Statistical analysis was done by two-tailed t-test and differences with a t-test value <0.05 were considered significant.

Three-fold experiments were set up and performed three times.

Figure 2:
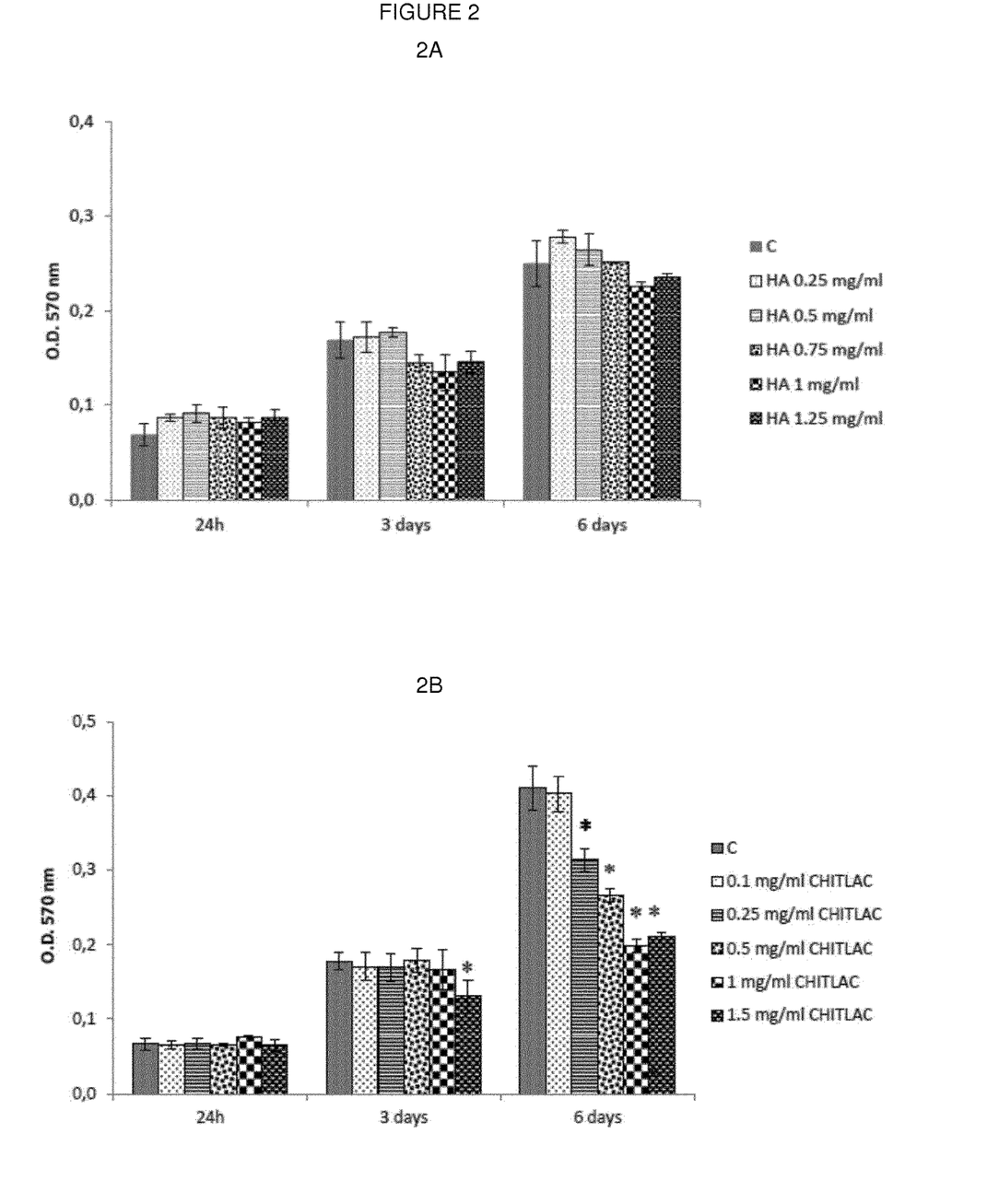
FIGS. 2A-2E. The figure shows the results obtained on the proliferation of human chondrocytes after incubation at 24 hours, 3 and 6 days with hyaluronic acid (HA), chitlac, hyaluronic acid and chitlac at different concentrations: (A) HA at the concentration from 0.25 to 1.25 mg/ml; (B) chitlac at the concentration from 0.1 to 1.5 mg/ml; (C) HA at the concentration of 0.5 mg/ml and chitlac at the concentration from 0.1 to 1.5 mg/ml; (D) HA at the concentration of 1.0 mg/ml and chitlac at the concentration from 0.1 to 1.0 mg/ml; (E) Ha at the concentration of 1.25 mg/ml and chitlac at the concentration from 0.1 to 1.0 mg/ml.

FIG. 2A and Table 2A show the results obtained on cell proliferation after incubation and 1, 3 and 6 days with hyaluronic acid at the mentioned concentrations.

TABLE 2A

|  | 24 hr | SD | 3 days | SD | 6 days | SD |
| --- | --- | --- | --- | --- | --- | --- |
| Ctrl | 0.069 | 0.012 | 0.169 | 0.019 | 0.250 | 0.024 |
| 0.25 mg/ml | 0.086 | 0.003 | 0.173 | 0.016 | 0.278 | 0.007 |
| 0.5 mg/ml | 0.091 | 0.009 | 0.177 | 0.005 | 0.264 | 0.017 |
| 0.75 mg/ml | 0.087 | 0.011 | 0.145 | 0.008 | 0.251 | 0.001 |
| 1 mg/ml | 0.081 | 0.006 | 0.135 | 0.019 | 0.226 | 0.005 |
| 1.25 mg/ml | 0.087 | 0.008 | 0.146 | 0.011 | 0.235 | 0.004 |

FIG. 2B and Table 2B show the results obtained on cell proliferation with chitlac at the mentioned concentrations.

TABLE 2B

|  | 24 hr | SD | 3 days | SD | 6 days | SD |
| --- | --- | --- | --- | --- | --- | --- |
| Ctrl | 0.066 | 0.008 | 0.178 | 0.011 | 0.426 | 0.020 |
| 0.1 mg/ml | 0.065 | 0.006 | 0.170 | 0.019 | 0.402 | 0.24 |
| 0.25 mg/ml | 0.067 | 0.007 | 0.169 | 0.018 | 0.313 | 0.014 |
| 0.5 mg/ml | 0.065 | 0.002 | 0.180 | 0.016 | 0.266 | 0.009 |
| 1 mg/ml | 0.076 | 0.008 | 0.166 | 0.026 | 0.199 | 0.009 |
| 1.5 mg/ml | 0.064 | 0.009 | 0.131 | 0.021 | 0.218 | 0.004 |

FIG. 2C and Table 2C show the results obtained on cell proliferation with hyaluronic acid at a concentration of 0.5 mg/ml and chitlac at concentrations increasing from 0.1 to 1.5 mg/ml at the mentioned concentrations.

TABLE 2C

| CHITLAC | 24 hr | SD | 3 days | SD | 6 days | SD |
| --- | --- | --- | --- | --- | --- | --- |
| Ctrl (0 mg) | 0.076 | 0.009 | 0.12 | 0.09 | 0.212 | 0.010 |
| 0.1 mg/ml | 0.081 | 0.007 | 0.132 | 0.001 | 0.179 | 0.024 |
| 0.25 mg/ml | 0.089 | 0.007 | 0.125 | 0.001 | 0.173 | 0.026 |
| 0.5 mg/ml | 0.094 | 0.005 | 0.0106 | 0.007 | 0.158 | 0.014 |
| 1 mg/ml | 0.085 | 0.005 | 0.0119 | 0.001 | 0.130 | 0.005 |
| 1.5 mg/ml | 0.087 | 0.007 | 0.097 | 0.007 | 0.115 | 0.010 |

FIG. 2D and Table 2D show the results obtained on cell proliferation with hyaluronic acid at a concentration of 1.0 mg/ml and chitlac at concentrations increasing from 0.1 to 1.0 mg/ml at the mentioned concentrations.

TABLE 2D

| CHITLAC | 24 hr | SD | 3 days | SD | 6 days | SD |
| --- | --- | --- | --- | --- | --- | --- |
| Ctrl (0 mg) | 0.085 | 0.003 | 0.173 | 0.008 | 0.23 | 0.016 |
| 0.1 mg/ml | 0.09 | 0.001 | 0.148 | 0.013 | 0.265 | 0.006 |
| 0.25 mg/ml | 0.094 | 0.007 | 0.165 | 0.007 | 0.267 | 0.008 |
| 0.5 mg/ml | 0.097 | 0.01 | 0.151 | 0.017 | 0.277 | 0.1019 |
| 0.75 mg/ml | 0.088 | 0.009 | 0.162 | 0.004 | 0.277 | 0.067 |
| 1.0 mg/ml | 0.092 | 0.01 | 0.154 | 0.015 | 0.232 | 0.585 |

FIG. 2E and Table 2E show the results obtained on cell proliferation with hyaluronic acid at a concentration of 1.25 mg/ml and chitlac at concentrations increasing from 0.1 to 1.0 mg/ml at the mentioned concentrations.

TABLE 2E

| CHITLAC | 24 hr | SD | 3 days | SD | 6 days | SD |
| --- | --- | --- | --- | --- | --- | --- |
| Ctrl (0 mg) | 0.089 | 0.006 | 0.149 | 0.005 | 0.29 | 0.003 |
| 0.1 mg/ml | 0.093 | 0.002 | 0.147 | 0.004 | 0.313 | 0.016 |
| 0.25 mg/ml | 0.099 | 0.015 | 0.176 | 0.008 | 0.312 | 0.004 |
| 0.5 mg/ml | 0.094 | 0.006 | 0.175 | 0.021 | 0.264 | 0.037 |
| 0.75 mg/ml | 0.100 | 0.041 | 0.176 | 0.019 | 0.271 | 0.008 |
| 1.0 mg/ml | 0.092 | 0.007 | 0.166 | 0.013 | 0.229 | 0.012 |

Example 3

Essay on Proliferation of Sinoviocytes From Human Synovia

Human synoviocytes were obtained from synovias of patients undergoing surgery to repair ligaments.

Cells were extracted by treatment with a first collagenase I solution of 40 U/ml for 12 hours in a 37° C. in incubator with a 5% $CO_2$ and 90% humidity percentage. The enzymatic action was blocked by adding the complete DMEM medium, the filtered and the 1200 rpm centrifuged solution. The pellet cells were re-suspended in DMEM, 10% fetal calf serum, 4 mM glutamine, 100 IU/ml penicillin/streptavidin and seeded on sterile culture plates in incubator at 37° C., with 5% $CO_2$ and relative humidity of 90%. The cell phenotype was confirmed by morphological analysis with optical microscopy and by immunocytochemical analysis for prolyl-4-hydroxylase. The medium was changed every two days and confluent cultures were detached with a 0.05% trypsin solution and 0.02% EDTA and passed into new plates by dividing them 1:3. For the experiments, cells from the fourth to sixth passage were used.

The synoviocytes were seeded at a concentration of 3000 cells per well in a 48-well plate. The day after the sowing, the cells were treated with the substances under study at the following concentrations: CTL 0.1 to 1 mg/ml; HA 0.1 to 1.25 mg/ml; a mixture of HA and CTL, consisting of a fixed concentration (0.5 mg/ml, 1 mg/ml or 1.25 mg/ml) of HA and variable amounts of CTL. The medium was renewed every two days with the substances under examination.

The effects of the treatment on cell viability were analyzed after 1 day, 3 days, 6 days by MTT (4-5-dimethylthiazol-2-yl)-2,5-diphenyltetrazolium bromide assay, according to the Denizot and Lang method as described in example 1.

In short, after removing the culture medium, the cell monolayers were washed with PBS and the MTT solution was added for 3 hours at 37° C. At the end of the incubation, the MTT was removed and replaced with an extraction solution (90% isopropanol, 10% DMSO) for 15 minutes at 37° C. The absorbance measurement was performed with a spectrophotometer at 570 nm.

Statistical analysis was done by two-tailed t-test and differences with a t-test value <0.05 were considered significant.

Three-fold experiments were set up and performed three times.

Figures 3, 3A:
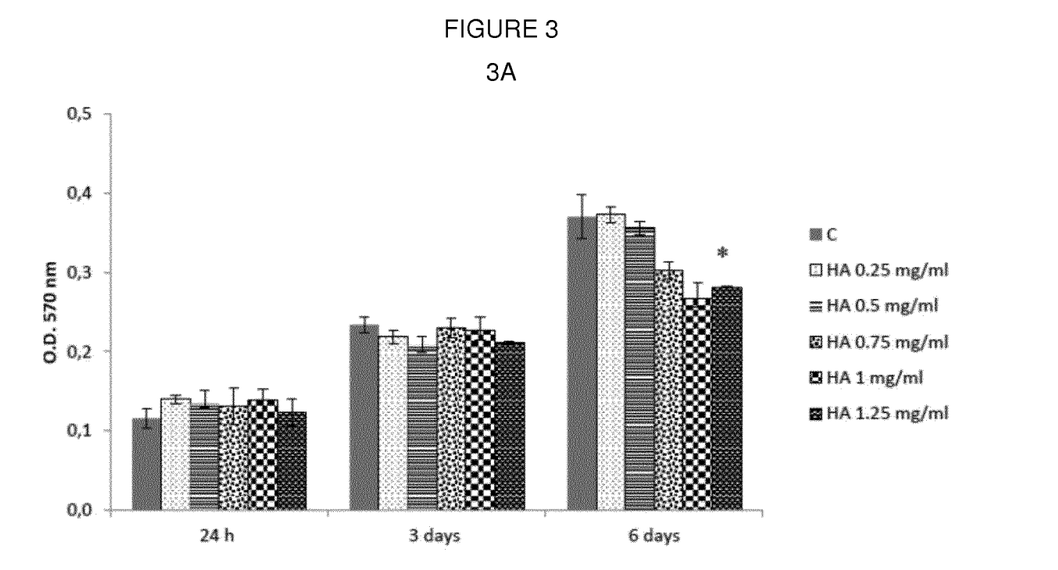
FIGS. 3A-3E. The figure shows the results obtained on the proliferation of human synoviocytes after incubation at 24 hours, 3 and 6 days with hyaluronic acid (HA), chitlac, hyaluronic acid and chitlac at different concentrations: (A) HA at the concentration from 0.25 to 1.25 mg/ml; (B) chitlac at the concentration from 0.1 to 1.5 mg/ml; (C) HA at the concentration of 0.5 mg/ml and chitlac at the concentration from 0.1 to 1.5 mg/ml; (D) HA at the concentration of 1.0 mg/ml and chitlac at the concentration from 0.1 to 1.0 mg/ml; (E) Ha at the concentration of 1.25 mg/ml and chitlac at the concentration from 0.1 to 1.0 mg/ml.
Figure 3:
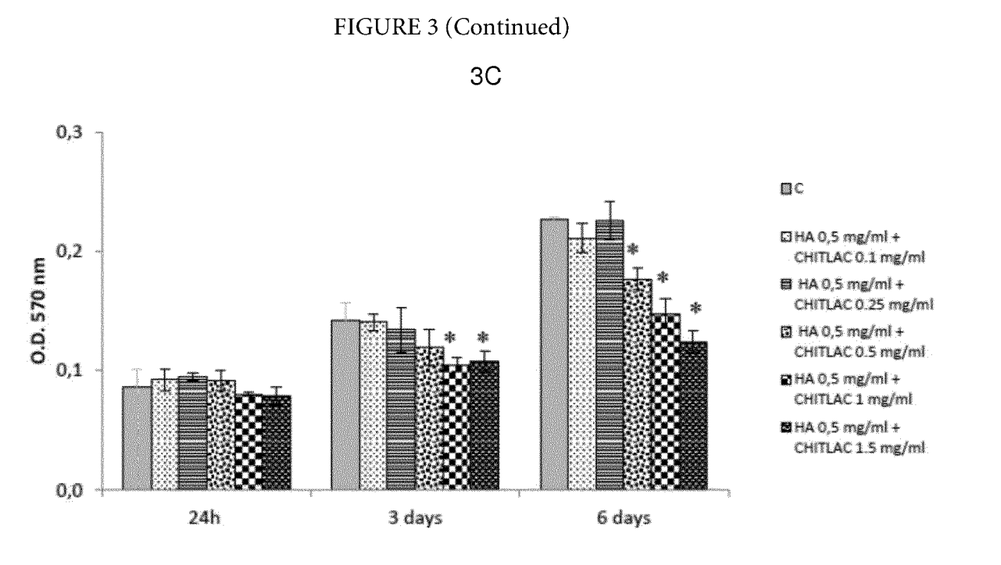

FIG. 3A and Table 3A show the results obtained on cell proliferation with hyaluronic acid at the mentioned concentrations.

TABLE 3A

|  | 24 hr | SD | 3 days | SD | 6 days | SD |
|---|---|---|---|---|---|---|
| Ctrl | 0.116 | 0.012 | 0.234 | 0.010 | 0.370 | 0.028 |
| 0.25 mg/ml | 0.140 | 0.005 | 0.218 | 0.009 | 0.373 | 0.010 |
| 0.5 mg/ml | 0.134 | 0.016 | 0.208 | 0.011 | 0.357 | 0.006 |
| 0.75 mg/ml | 0.132 | 0.023 | 0.229 | 0.012 | 0.302 | 0.011 |
| 1 mg/ml | 0.139 | 0.014 | 0.227 | 0.016 | 0.274 | 0.023 |
| 1.25 mg/ml | 0.124 | 0.018 | 0.211 | 0.003 | 0.280 | 0.003 |

FIG. 3B and Table 3B show the results obtained on cell proliferation with chitlac at the mentioned concentrations.

TABLE 3B

|  | 24 hr | SD | 3 days | SD | 6 days | SD |
|---|---|---|---|---|---|---|
| Ctrl | 0.090 | 0.005 | 0.183 | 0.015 | 0.319 | 0.005 |
| 0.1 mg/ml | 0.096 | 0.007 | 0.195 | 0.020 | 0.303 | 0.023 |
| 0.25 mg/ml | 0.092 | 0.006 | 0.154 | 0.011 | 0.282 | 0.020 |
| 0.5 mg/ml | 0.087 | 0.007 | 0.132 | 0.011 | 0.257 | 0.004 |
| 1 mg/ml | 0.093 | 0.012 | 0.114 | 0.011 | 0.184 | 0.008 |
| 1.5 mg/ml | 0.087 | 0.009 | 0.117 | 0.002 | 0.166 | 0.026 |

FIG. 3C and Table 3C show the results obtained on cell proliferation with hyaluronic acid at a concentration of 0.5 mg/ml and chitlac at concentrations increasing from 0.1 to 1.5 mg/ml at the mentioned concentrations.

TABLE 3C

| CHITLAC | 24 hr | SD | 3 days | SD | 6 days | SD |
|---|---|---|---|---|---|---|
| Ctrl (0 mg) | 0.086 | 0.016 | 0.142 | 0.014 | 0.227 | 0.003 |
| 0.1 mg/ml | 0.092 | 0.009 | 0.141 | 0.007 | 0.211 | 0.012 |
| 0.25 mg/ml | 0.095 | 0.003 | 0.134 | 0.019 | 0.226 | 0.016 |
| 0.5 mg/ml | 0.091 | 0.001 | 0.120 | 0.015 | 0.177 | 0.009 |
| 1 mg/ml | 0.080 | 0.001 | 0.105 | 0.006 | 0.148 | 0.012 |
| 1.5 mg/ml | 0.079 | 0.007 | 0.107 | 0.008 | 0.124 | 0.009 |

FIG. 3D and Table 3D show the results obtained on cell proliferation with hyaluronic acid at a concentration of 1.0 mg/ml and chitlac at increasing concentrations at the mentioned concentrations.

TABLE 3D

| CHITLAC | 24 hr | SD | 3 days | SD | 6 days | SD |
|---|---|---|---|---|---|---|
| Ctrl (0 mg) | 0.102 | 0.003 | 0.224 | 0.013 | 0.487 | 0.001 |
| 0.1 mg/ml | 0.109 | 0.001 | 0.217 | 0.006 | 0.46 | 0.014 |
| 0.25 mg/ml | 0.108 | 0.001 | 0.202 | 0.008 | 0.410 | 0.007 |
| 0.5 mg/ml | 0.107 | 0.006 | 0.211 | 0.012 | 0.401 | 0.011 |
| 0.75 mg/ml | 0.113 | 0.009 | 0.208 | 0.012 | 0.367 | 0.023 |
| 1 mg/ml | 0.104 | 0.007 | 0.205 | 0.007 | 0.372 | 0.010 |

Figure 3E:
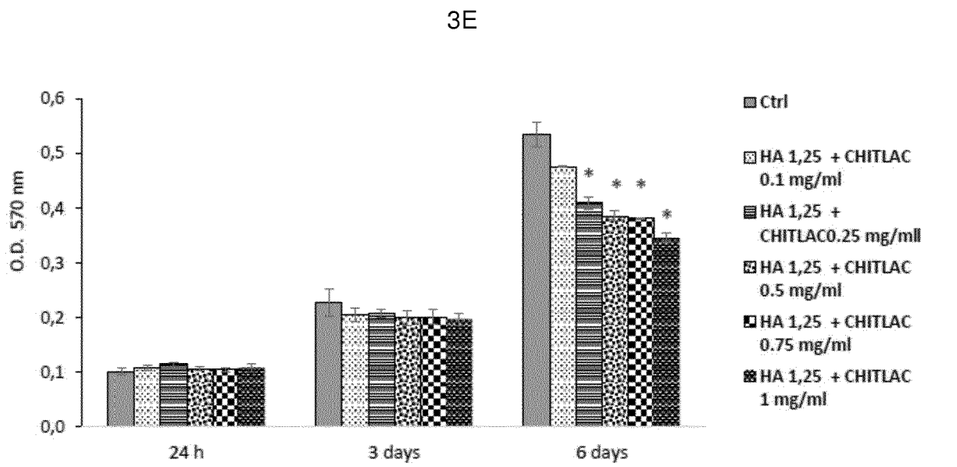

FIG. 3E and Table 3E show the results obtained on cell proliferation with hyaluronic acid at a concentration of 1.25 mg/ml and chitlac at increasing concentrations at the mentioned concentrations.

TABLE 3E

| CHITLAC | 24 hr | SD | 3 days | SD | 6 days | SD |
|---|---|---|---|---|---|---|
| Ctrl (0 mg) | 0.101 | 0.006 | 0.228 | 0.024 | 0.535 | 0.021 |
| 0.1 mg/ml | 0.108 | 0.005 | 0.206 | 0.013 | 0.476 | 0.002 |
| 0.25 mg/ml | 0.114 | 0.004 | 0.208 | 0.007 | 0.409 | 0.011 |
| 0.5 mg/ml | 0.106 | 0.003 | 0.199 | 0.013 | 0.385 | 0.008 |
| 0.75 mg/ml | 0.104 | 0.003 | 0.201 | 0.013 | 0.381 | 0.001 |
| 1 mg/ml | 0.108 | 0.008 | 0.197 | 0.011 | 0.346 | 0.008 |

Example 4

Assay on Migration of Dermal Fibroblasts In Vitro—Scratch Test

The influence of the treatment with HA and CTL on migration and proliferation speed of cultured fibroblasts was evaluated on cells prepared as described in Example 1 and brought to semi-confluence on 6-well cell culture plates. The cell monolayer was cut to divide it into two parts and then treated with the studied substances alone (HA at a concentration of 1 mg/ml; CTL at a concentration of 0.75 mg/ml) or with the mixture of 1 Mg/ml HA and CTL at a concentration of 0.75 mg/ml). Closure of the gap created in the cell monolayer was monitored at the optical microscope 48 and 72 hours after treatment. Three-fold experiments were set up and performed three times.

Figures 4, 4A:
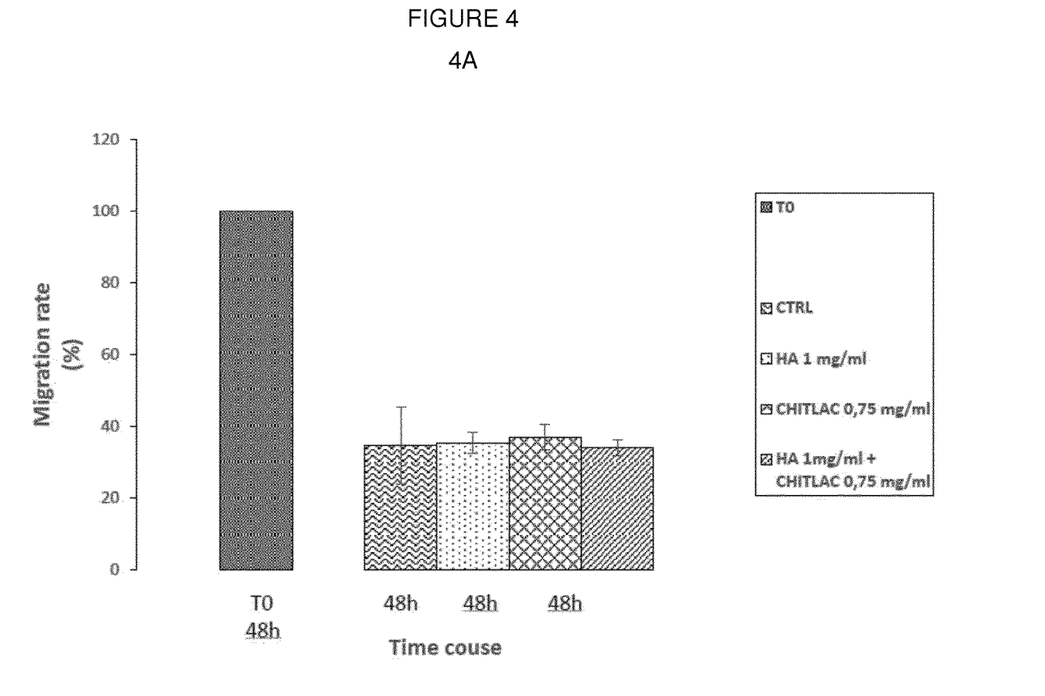

The results obtained are shown in FIG. 4A as % of the cell migration speed in time, while in FIG. 4B the results are reported as cut closing process in μm in time after 0.48 and 72 hours.

The invention claimed is:

1. A method of tissue repairing through promoting cell proliferation of chondrocytes and through inhibiting cell proliferation of fibroblasts and synoviocytes, the method comprising the step of administering to patients in need thereof a therapeutically effective amount of a polysaccharide composition comprising hyaluronic acid and an oligosaccharide derivative of chitosan obtained by a reductive amination reaction of D-glucosamine with lactose, said D-glucosamine having a degree of substitution of the amine functional group with lactose of at least 40%, wherein the hyaluronic acid is in the range lactose is in the range comprised from 0.25 to 0.75% by weight, the hyaluronic acid has an average molecular weight of between 1,000 and 1.600 kDa and the chitosan, of the oligosaccharide derivative of chitosan with lactose, has an average molecular weight of between 200 and 400 kDa.

2. The method according to claim 1, wherein the hyaluronic acid is a matrix in which the oligosaccharide derivative of chitosan with lactose is homogeneously dispersed.

3. The method according to claim 1, wherein the hyaluronic acid is 1% by weight.

4. The method according to claim 1, wherein the hyaluronic acid is 1.25% by weight.

5. The method according to claim 3, wherein the oligosaccharide derivative of chitosan with lactose is 0.25% by weight.

6. The method according to claim 3, wherein the oligosaccharide derivative of chitosan with lactose is 0.5% by weight.

7. The method according to claim 3, wherein the oligosaccharide derivative of chitosan with lactose is 0.5% by weight.

8. The method according to claim 1, wherein the oligosaccharide derivative of chitosan with lactose has a degree of substitution comprised from 50 to 70%.

9. The method according to claim 1, wherein the oligosaccharide derivative of chitosan with lactose has a degree of substitution of 60%.

10. The method according to claim 1, wherein the use is in traumatic and/or post-surgical tissue process and/or chronic fibrotic processes associated to autoimmune diseases.

11. The method according to claim 10, wherein the use is in traumatic and post-surgical sequelae involving dermis and abdominal tissues.

12. The method according to claim 10, wherein the use is in post-surgical sequelae of tendon and/or cartilage tissues.

13. The method according to claim 10, wherein the use is in fibrotic process associated to autoimmune diseases affecting dermis and/or cartilage tissues.

14. The method according to claim 13, wherein the use is in psoriasis and psoriatic osteoarthritis.

15. Biomaterials in forms of aqueous solutions, non-woven fabric, membranes, hydrogels or preparations obtained thereof by freeze-drying, said biomaterials comprising a polysaccharide composition comprising hyaluronic acid and an oligosaccharide derivative of chitosan obtained by a reductive amination reaction of D-glucosamine with lactose, said D-glucosamine having a degree of substitution of the amine functional group with lactose of at least 40%, wherein the hyaluronic acid is in the range comprised from 1 to 1.25% by weight, the oligosaccharide derivative of chitosan with lactose is in the range comprised from 0.25 to 0.75% by weight, the hyaluronic acid has an average molecular weight of between 1,000 and 1,600 kDa and the chitosan, of the oligosaccharide derivative of chitosan with lactose, has an average molecular weight of between 200 and 400 kDa.

* * * * *